(12) United States Patent
Jiang et al.

(10) Patent No.: US 11,514,812 B2
(45) Date of Patent: Nov. 29, 2022

(54) AUTONOMOUS PHYSICAL ACTIVITY ASSISTANCE SYSTEMS AND METHODS THEREOF

(71) Applicant: Pinegem Technologies LLC, Short Hills, NJ (US)

(72) Inventors: Wenhai Jiang, Short Hills, NJ (US); George Jiang, Short Hills, NJ (US); Margaret Zhu, Short Hills, NJ (US)

(73) Assignee: PINEGEM TECHNOLOGIES LLC, Short Hills, NJ (US)

( * ) Notice: Subject to any disclaimer, the term of this patent is extended or adjusted under 35 U.S.C. 154(b) by 1095 days.

(21) Appl. No.: 16/148,596

(22) Filed: Oct. 1, 2018

(65) Prior Publication Data

US 2019/0304334 A1    Oct. 3, 2019

Related U.S. Application Data

(60) Provisional application No. 62/761,635, filed on Apr. 2, 2018.

(51) Int. Cl.
*G09B 19/00* (2006.01)
*A61B 5/021* (2006.01)
(Continued)

(52) U.S. Cl.
CPC .......... *G09B 19/003* (2013.01); *A61B 5/0022* (2013.01); *A61B 5/0077* (2013.01);
(Continued)

(58) Field of Classification Search
CPC .............. G09B 19/003; G09B 19/0038; A61B 5/0022; A61B 5/0077; A61B 5/021; A61B 5/1071; A61B 5/1112; A61B 5/14532; A61B 5/14542; A61B 5/0205; A61B 5/02; A61B 2503/10; G06N 3/02; G06N 7/02; G06N 20/00; G06N 3/008; G16H 20/30
(Continued)

(56) References Cited

U.S. PATENT DOCUMENTS 10,489,649 B2 * 11/2019 Shaw ................... A61B 8/4427
10,722,775 B2 *  7/2020 Black ................. A63B 71/0686
(Continued)

*Primary Examiner* — Anh V La
(74) *Attorney, Agent, or Firm* — Metis IP LLC

(57) ABSTRACT

The present disclosure relates to systems and methods for automatically assisting physical activities. The system may include a body condition monitoring unit, and an autonomous companion unit. The body condition monitoring unit may obtain body condition data of a user. The autonomous companion unit may be automatically move alongside the user and guide the user. The autonomous companion unit may include a transporting subunit, a plurality of sensors, and a controller subunit. The transporting subunit may be enable the movement of the autonomous companion unit. The plurality of sensors may obtain surroundings data associated with the autonomous companion unit. The controller subunit may control the transporting subunit to move the autonomous companion unit according to a target movement plan. The target movement plan may include a target route and a target speed profile, which are based on a preliminary movement plan, the surroundings data, and the body condition data.

20 Claims, 7 Drawing Sheets

(51) Int. Cl.
 *A61B 5/145* (2006.01)
 *A61B 5/00* (2006.01)
 *A61B 5/11* (2006.01)
 *A61B 5/107* (2006.01)

(52) U.S. Cl.
 CPC ............ *A61B 5/021* (2013.01); *A61B 5/1071* (2013.01); *A61B 5/1112* (2013.01); *A61B 5/14532* (2013.01); *A61B 5/14542* (2013.01)

(58) Field of Classification Search
 USPC ............ 434/257; 340/573.1, 540, 522, 686.1
 See application file for complete search history.

(56) References Cited

U.S. PATENT DOCUMENTS

| | | | |
|---|---|---|---|
| 11,016,491 B1* | 5/2021 | Millard | G05D 1/0274 |
| 11,161,236 B2* | 11/2021 | Mallinson | G05D 1/0094 |
| 2003/0172282 A1 | 9/2003 | Jiang | |
| 2018/0085928 A1* | 3/2018 | Yamato | B25J 11/001 |

* cited by examiner

AUTONOMOUS PHYSICAL ACTIVITY ASSISTANCE SYSTEMS AND METHODS THEREOF

CROSS-REFERENCE TO RELATED APPLICATIONS

This application claims priority to U.S. Provisional Application No. 62/761,635, filed on Apr. 2, 2018, the contents of which is hereby incorporated by reference.

TECHNICAL FIELD

The present disclosure generally relates to systems and methods for autonomously assisting physical activities of a user, and in particular, to systems and methods for guide the user to perform certain physical activities, such as but not limited to running exercises.

BACKGROUND

In certain situations, a person may perform physical activities for purposes such as but not limited to personal health, work, leisure, and entertainment. In some cases, the physical activities are performed with a defined goal. However, sometimes it can be difficult for the person to achieve the goal. On the one hand, the person may not know how to precisely control himself/herself to perform the physical activity according to the defined goal. On the other hand, the person may give up before achieving the defined goal due to physical hardships or that the goal is unreasonable in the first place. In addition, in some cases, during the physical activity, the surrounding environment and the person's physical conditions may change, making it impossible to achieve the goal. Taking running as an example, the defined goal may include a goal distance, a goal time, a goal speed, etc. During the running, the person may not know how to precisely control himself/herself to keep the goal speed or reach the goal distance. Additionally or alternatively, the person may be forced to give up because he/she runs too fast at the beginning, the goal speed is set too high, or that the surroundings environment changes (e.g. rain). Therefore, it is desirable to provide systems and methods for automatically assist the user to perform the physical activity reasonably, efficiently, and with the possibility of instant adjustments, so as to achieve the defined goal.

SUMMARY

In one aspect of the present disclosure, an autonomous physical activity assistance system is provided. The system may include a body condition monitoring unit configured to obtain body condition data of a user and an autonomous companion unit that is configured to automatically move alongside the user and guide the user. The autonomous companion unit may include a transporting subunit configured to enable the movement of the autonomous companion unit; a plurality of sensors physically connected to the transporting subunit, and configured to obtain surroundings data associated with the autonomous companion unit; a controller subunit in communication with the transporting subunit, the plurality of sensors, and the body condition monitoring unit, and configured to: receive the surroundings data from the plurality of sensors; wirelessly receive the body condition data from the body condition monitoring unit; and control the transporting subunit to move the autonomous companion unit according to a target movement plan, the target movement plan including a target route and a target speed profile, which are based on a preliminary movement plan, the surroundings data, and the body condition data In some embodiments, the system may also include a physical activity management unit, configured to: provide the preliminary movement plan, which includes a preliminary route and a preliminary speed profile.

In some embodiments, the surroundings data and the body condition data may be obtained in real-time.

In some embodiments, the controller subunit may be also configured to adjust the preliminary route and the preliminary speed profile in real-time to provide the target route and target speed profile based on the surroundings data and the body condition data.

In some embodiments, the physical activity management unit may be also configured to store the target movement plan in a database.

In some embodiments, the plurality of sensors may include at least two or more of: a GPS sensor, an odometry sensor, a depth camera, or an angle sensor.

In some embodiments, the controller subunit or the physical activity management unit may be also configured to determine a speed of the autonomous companion unit based on the surroundings data; and the physical activity management unit may be configured to determine the target movement plan based on the speed of the autonomous companion unit, the surroundings data and the body condition data.

In some embodiments, the controller unit or the physical activity management unit may be also configured to generate a digital map of an area surrounding the autonomous companion unit based on the surroundings data.

In some embodiments, the autonomous companion unit may also include an interaction subunit, which is configured to display contents including the digital map.

In some embodiments, the interaction subunit may be also configured to interact with the user to inform the user about the target movement plan.

In some embodiments, the controller subunit may be also configured to receive user instructions from the user through the interaction subunit.

In some embodiments, the controller subunit may be also configured to determine the target movement plan based on the preliminary movement plan, the surroundings data, the body condition data, and the user instruction.

In some embodiments, the controller subunit may be also configured to transmit the user instruction to the physical activity management unit.

In some embodiments, the body condition data may include at least one of a heart rate, a blood pressure, a blood oxygen level, or a blood sugar level.

In some embodiments, the physical activity management unit may be configured to: obtain personal information of the user, the personal information of the user including at least one of an age, a height, a weight, or a gender of the user; obtain a template movement plan based on the personal information of the user; determine a template body condition data corresponding to the template movement plan based on the personal information of the user; compare the template body condition data with the body condition data; and determine the preliminary movement plan based on the comparison result between the template body condition data and the body condition data.

In some embodiments, the controller subunit may include a mobile device.

In another aspect of the present disclosure, a method is provided. The method may be implemented on a computing device having at least one processor, at least one storage medium, and a communication platform connected to a network. The method may include automatically moving an autonomous companion unit alongside a user and guide the user according to a target movement plan. The target movement plan may include a target route and a target speed profile. The target movement plan may be determined by: receiving surroundings data associated with the user from a plurality of sensors of the autonomous companion unit; receiving body condition data associated with the user from a body condition monitoring unit; and determining the target movement plan based on a preliminary movement plan, the surroundings data, and the body condition data.

In some embodiments, the method may also include providing a preliminary movement plan by a physical activity management unit, which includes a preliminary route and a preliminary speed profile.

In some embodiments, the method may also include providing a preliminary movement plan by a physical activity management unit, which includes a preliminary route and a preliminary speed profile.

In some embodiments, the method may also include receiving the surroundings data and the body condition data in real-time.

In some embodiments, the method may also include adjusting the preliminary route and the preliminary speed profile in real-time to provide the target route and target speed profile based on the surroundings data and the body condition data.

In some embodiments, the method may also include storing the target movement plan in a database by the physical activity management unit.

In some embodiments, the plurality of sensors may include at least two or more of: a GPS sensor, an odometry sensor, a depth camera, or an angle sensor.

In some embodiments, the method may also include determining a speed of the autonomous companion unit based on the surroundings data by the physical activity management unit; determining the target movement plan based on the speed of the autonomous companion unit, the surroundings data and the body condition data by the physical activity management unit In some embodiments, the method may also include generating a digital map of an area surrounding the autonomous companion unit based on the surroundings data by the controller unit or the physical activity management unit.

In some embodiments, the method may also include displaying contents including the digital map by an interaction unit of the autonomous companion unit.

In some embodiments, the method may also include receiving user instructions from the user through the interaction subunit by the controller subunit interacting with the user to inform the user about the target movement plan by the interaction unit.

In some embodiments, the method may also include determining the target movement plan based on the preliminary movement plan, the surroundings data, the body condition data, and the user instruction by the controller subunit.

In some embodiments, the method may also include transmitting the user instruction to the physical activity management unit by the controller subunit.

In some embodiments, the body condition data may include at least one of a heart rate, a blood pressure, a blood oxygen level, or a blood sugar level In some embodiments, the method may also include obtaining personal information of the user, the personal information of the user including at least one of an age, a height, a weight, or a gender of the user; obtaining a template movement plan based on the personal information of the user; determining a template body condition data corresponding to the template movement plan based on the personal information of the user; comparing the template body condition data with the body condition data; and determining the preliminary movement plan based on the comparison result between the template body condition data and the body condition data.

In some embodiments, the controller subunit may include a mobile device.

In another aspect of the present disclosure, a non-transitory computer readable medium is provided. The non-transitory computer readable medium may include executable instructions that, when executed by at least one processor, directs the at least one processor to perform a method. The method may include automatically moving an autonomous companion unit alongside a user and guide the user according to a target movement plan. The target movement plan may include a target route and a target speed profile. The target movement plan may be determined by: receiving surroundings data associated with the user from a plurality of sensors of the autonomous companion unit; receiving body condition data associated with the user from a body condition monitoring unit; and determining the target movement plan based on a preliminary movement plan, the surroundings data, and the body condition data.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
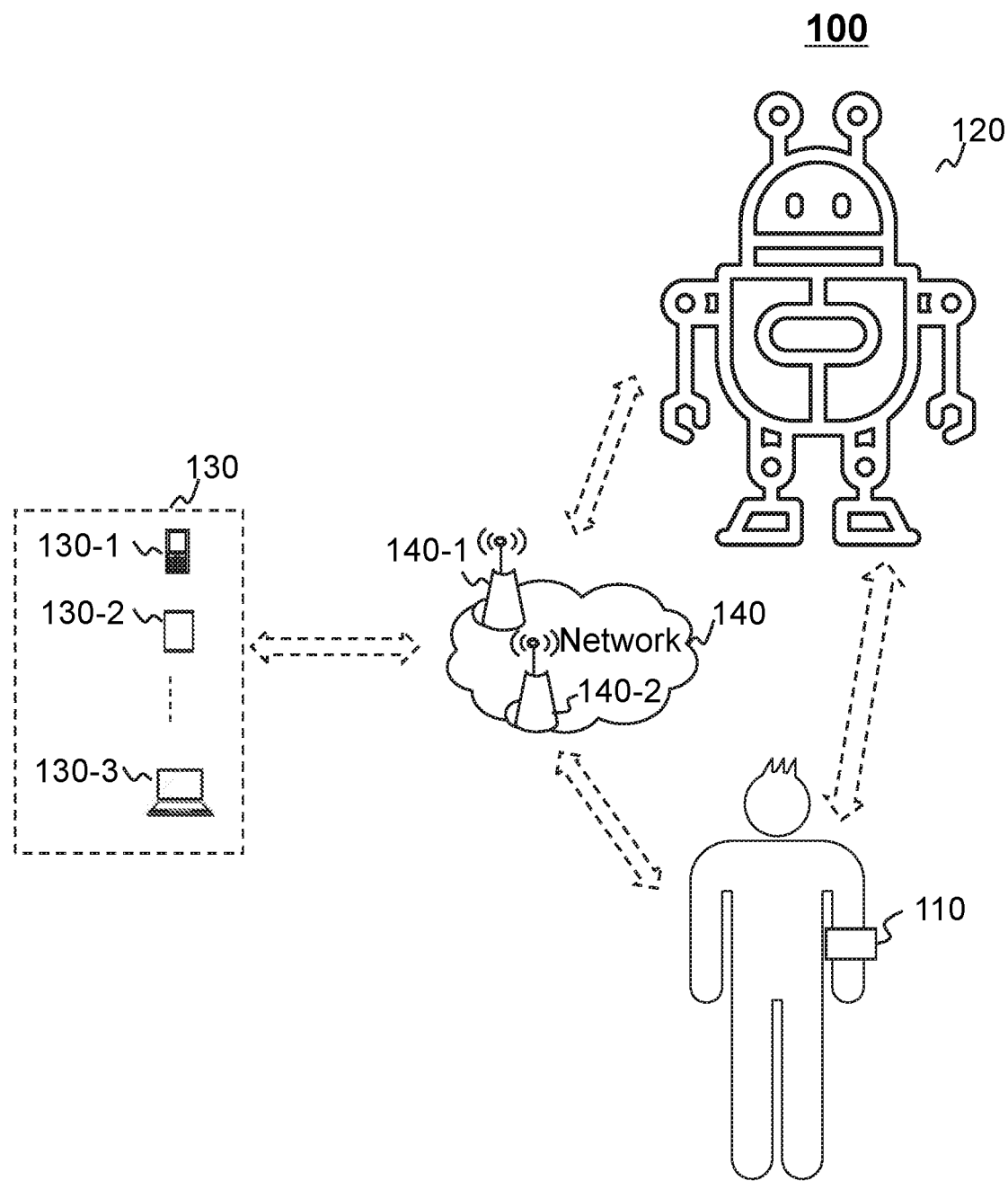
FIG. 1 is a schematic diagram illustrating an exemplary physical activity assistance system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowchart may be implemented not in order. Conversely, the operations may be implemented in inverted order, or simultaneously. Moreover, one or more other operations may be added to the flowcharts. One or more operations may be removed from the flowcharts.

The positioning technology used in the present disclosure may be based on a global positioning system (GPS), a global navigation satellite system (GLONASS), a compass navigation system (COMPASS), a Galileo positioning system, a quasi-zenith satellite system (QZSS), a wireless fidelity (WiFi) positioning technology, or the like, or any combination thereof. One or more of the above positioning systems may be used interchangeably in the present disclosure.

An aspect of the present disclosure relates to physical activity assistance systems and methods thereof. The physical activity assistance systems and method may include automatically controlling an autonomous companion unit to move alongside a user and guide the user based on a target movement plan. Taking running as an example, the target movement plan may include a target route and speeds corresponding to different segments of the target route. When the user performs the physical activity in companion with the autonomous companion unit 120 according to the target movement plan, the physical activity assistance method may also include tracking performance information of the user. For running, the physically activity assistance system may be called an autonomous running companion suite (ARCS).

It should be noted that while assisting/guiding the user to exercise (e.g. run) is illustrated as an example for the present disclosure, the optimization of other types of physical activities that relate to pattern (e.g. route) control and/or speed control can also utilize the methods and systems herein disclosed. For example, the other types of physical activities may include swimming, skiing, automobile racing, boating, etc.

FIG. 1 is a schematic diagram illustrating an exemplary physical activity assistance system according to some embodiments of the present disclosure. As used herein, the physical activity may be any physical activity that relates to pattern (e.g. route) control and/or speed control, e.g., jogging, running, swimming, skiing, automobile racing, boating, etc. In some embodiments, the physical activity assistance system 100 may include a body condition monitoring unit 110, an autonomous companion unit 120, a physical activity management unit 130, and a network 140. For running, the physical activity assistance system 100 may be called an autonomous running companion suite (ARCS). The body condition monitoring unit 110 may be called a unit for implementing a runner tracking service (RTS). The autonomous companion unit 120 may be called an autonomous running companion (ARC). The physical activity management unit 130 may be called a unit for implementing a runner management service (RMS).

The body condition monitoring unit 110 may be configured to obtain body condition data of a user. The body condition data may indicate a physiological condition of the user. For example, the body condition data may include a heart rate, a blood pressure, a blood oxygen level, a blood sugar level, etc. In some embodiments, the body condition monitoring unit 110 may obtain the body condition data of the user in real-time and display the body condition data through an interface (not shown in FIG. 1) of the body condition monitoring unit 110. The body condition data may include preliminary body condition data when the user performs the physical activity, and target body condition data when the user performs the physical activity according to a target movement plan. In some embodiments, the body condition monitoring unit 110 may further store the body condition data in a storage medium of the body condition monitoring unit 110.

In some embodiments, in order to obtain the body condition data of the user, the body condition monitoring unit 110 may be directly in touch with the user as shown in FIG. 1, or may be not in touch with the user. In some embodiments, the body condition monitoring unit 110 may include a plurality of biometric sensors to measure the body condition data of the user in real-time. For example, the plurality of biometric sensors may include a heart rate sensor (e.g., an optical transceiver), a blood pressure sensor (e.g., a photo plethysmography (PPG) sensor), a blood oxygen sensor (e.g., a pulse oximeter sensor), or the like, or any combination thereof.

In some embodiments, the body condition monitoring unit 110 may be in communication with one or more components of the physical activity assistance system 100 (e.g., the autonomous companion unit 120, or the physical activity management unit 130) via the network 140. For example, the body condition monitoring unit 110 may transmit the body condition data to the autonomous companion unit 120 or the physical activity management unit 130 via the network 140.

In some embodiments, the body condition monitoring unit 110 may be a wearable device carried by the user, which may be used to monitor the body condition of the user. For example, the wearable device may include a smart bracelet, a smart footgear, a smart glass, a smart helmet, a smart watch, a smart clothing, a smart backpack, a smart accessory, or the like, or any combination thereof.

The autonomous companion unit 120 may be configured to automatically move alongside the user. In some embodiments, the autonomous companion unit 120 may be only in companion with the user, i.e., the autonomous companion unit 120 may not intervene the user to perform the physical activity. For example, if the user runs, the autonomous companion unit 120 may move alongside the user or run with the user. In some embodiments, such an approach may prevent the user from feeling lonely so that the user can persist with the physical activity. In some embodiments, such an approach may provide real-time updated activity plans to the user. In some embodiments, the autonomous companion unit 120 may further encourage, praise, prize, evaluate, or critic the user based on the performance of the user.

In some embodiments, the autonomous companion unit 120 may guide the user to perform the physical activity. For example, if the user plans to run, the autonomous companion unit 120 may run ahead of the user, beside the user, behind the user, or change its positions intermittently (but within short distance) and guide the user to run. In some embodiments, the autonomous companion unit 120 may guide the user to perform the physical activity based on a target movement plan. The autonomous companion unit 120 may perform the physical activity according to the target movement plan, and the user may also perform the physical activity according to the target movement plan by following the autonomous companion unit 120. In some embodiments, the target movement plan may represent a defined goal that the user desires to achieve when performing the physical activity. As used herein, taking running as an example, the target movement plan may include a target route and a target speed profile. The target route may refer to a route along which a user performs a physical activity. The target speed profile may include a plurality of speeds corresponding to different segments of the target route. In some embodiments, the autonomous companion unit 120 may run along the target route with the speed profile, and the user may run along the target route with the speed profile by following the autonomous companion unit 120.

Figure 2:
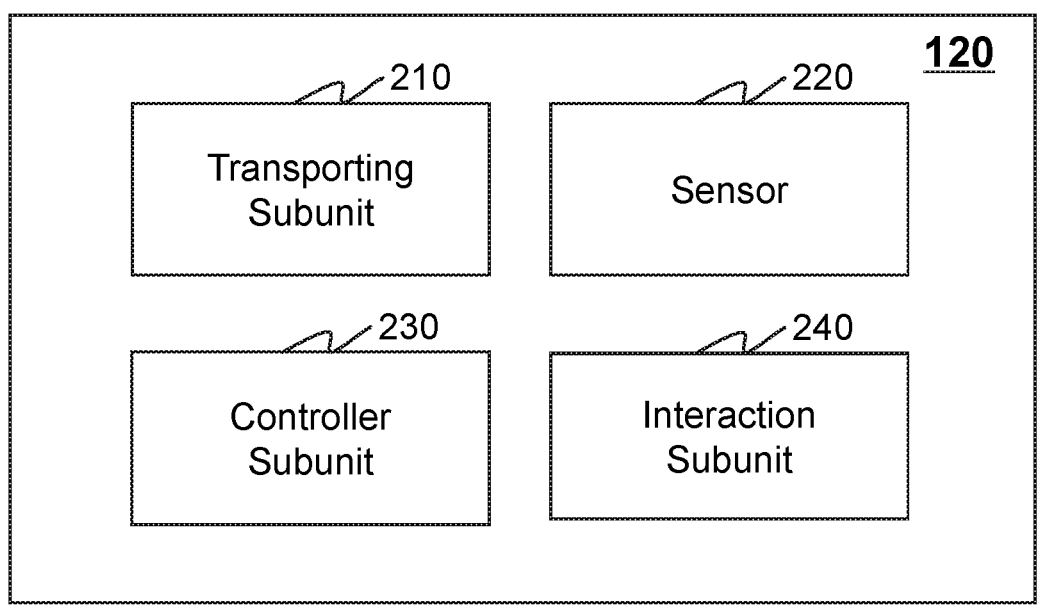
FIG. 2 is a block diagram illustrating an exemplary autonomous companion unit according to some embodiments of the present disclosure.

In some embodiments, a controller subunit (e.g., the controller subunit 230 as illustrated in FIG. 2) may automatically move the autonomous companion unit 120 according to the target movement plan by controlling data associated with the autonomous companion unit 120. The data may include a speed, a location, a direction, a strength of the autonomous companion unit 120, etc. In some embodiments, the controller subunit 230 may obtain the data in real-time, and compare the data with predetermined data when the autonomous companion unit 120 moves according to the target movement plan. In response to a determination that the data do not match the predetermined data, the controller subunit 230 may adjust the data to the predetermined data in real-time, thereby making sure the autonomous companion unit 120 move according to the target movement plan.

In some embodiments, the autonomous companion unit 120 may automatically move according to the target movement plan based on a control technique. The control technique may include a PID (proportional-integral-derivative) control technique, a PD (proportional-derivative) control technique, a PI (proportional-integral) control technique, neural network control techniques, a self-adaptive control technique, a variable structure control technique, a fuzzy control technique, or the like, or any combination thereof.

The autonomous companion unit 120 may receive surroundings data associated with the user as the user performs a physical activity. The surroundings data may represent a practical scenario where the user performs the physical activity. In some embodiments, the surroundings data may include preliminary surroundings data when the user performs the physical activity, and target surroundings data when the user performs the physical activity according to a target movement plan. Taking running as an example, the surroundings data associated with the user may include data of surroundings objects associated with the user, environmental information associated with the surroundings. For example, the surroundings objects may include roads, traffic lights, traffic signs, temporary road blocks, pedestrians, landmarks, vehicles, trees, buildings, rivers, bridges, or the like, or any combination thereof. The environmental information may include weather (e.g., sunny, rainy, snowy), visibility conditions, traffic condition, wind speeds, time of day, etc. In some embodiments, the data of the surroundings object may include a location of the surroundings object, a dimension of the surroundings object, an outline of the surroundings object and any other feature information used for representing the surroundings object. Taking a road as an example, the data of each may include a direction of a road, a length of a load, a width of a road, a center line of a road, a border line of the road, an intersection of the road, a turning (e.g., a right turning, a left turning) of a road, a slope of a road, an angle of inclination of a slope, or the like, or any combination. It should be noted that the term "road" herein used may refer to any type of road (e.g. paved road, sidewalk or dirt road) or any route according to which a runner can pass. In some embodiments, the road refers to a route outside an area specific designed for exercising or racing (e.g. not in a track field or stadium).

In some embodiments, the autonomous companion unit 120 may receive surroundings data associated with the user from a plurality of sensors of the autonomous companion unit 120. In some embodiments, the plurality of sensors may be mounted on the autonomous companion unit 120 or the physical activity management unit 130. If the plurality of sensors may be mounted on the autonomous companion unit 120, the plurality of sensors may obtain surroundings data associated with the autonomous companion unit 120. Taking running as an example, since the autonomous companion unit 120 may run in companion with the user, the surroundings data associated with the autonomous companion unit 120 may be similar to the surroundings data associated with the user. Therefore, the surroundings data obtained by the plurality of sensors may be considered as the surroundings data associated with the user. If the plurality of sensors are mounted on the physical activity management unit 130, the physical activity management unit 130 may transmit the surroundings data to the autonomous companion unit 120 via the network 150.

The plurality of sensors may include a GPS sensor, an odometry sensor, an angle sensor, a depth camera, a high-definition camera, a Light Detection And Ranging (LiDAR), or the like, or the any combination thereof. In some embodiments, the odometry sensor add/or the GPS sensor may be used to determine a relative distance to the surroundings object and locate the surroundings object. The depth camera, the high-definition camera may be used to obtain images of the surroundings object. The LiDAR may be used to obtain point clouds (e.g., three-dimensional representation) associated with the surroundings object. Therefore, the surroundings data associated with the autonomous companion unit 120 may then be determined by the plurality of sensors.

In some embodiments, the controller subunit 230 may generate a digital map of an area surrounding the autonomous companion unit 120 and/or the user at least based on the surroundings data. The digital map may represent the practical scenario where the user performs the physical activity. In some embodiments, the digital map may display the surroundings data associated with the user.

In some embodiments, the autonomous companion unit 120 may determine the target movement plan based on the target body condition data, the target surroundings data and a preliminary movement plan. The preliminary movement plan may include a preliminary route and a preliminary speed profile. The preliminary movement plan may be customized for the user or by others (e.g. a trainer of the user). In some embodiments, the preliminary movement plan may be determined based on personal information of the user, the preliminary body condition data when the user performs the physical activity and preliminary surroundings data when the user performs the physical activity. For example, the personal information may include an age, a height, a weight, a gender, an occupation, a recorded proficiency when the user performs the physical activity, etc.

In some embodiments, the target body condition data and/or the target surroundings data may be different from the preliminary body condition data obtained in 520 and/or the preliminary surroundings data respectively. The controller subunit 230 may automatically adjust the preliminary movement plan based on the difference. Alternatively, the controller subunit 230 may display the difference via an interface of the autonomous companion unit 120 or transmit the difference to the body condition monitoring unit 110 or the physical activity management unit 130, and the user may determine whether to adjust the preliminary movement plan based on the difference.

In some embodiments, the controller subunit 230 may determine the target movement plan further based on target user inputs. For example, the target user inputs may include inputting a target value, inputting a target speed profile, etc.

In some embodiments, the autonomous companion unit 120 may determine a plurality of target movement plans. For example, an overall length of each target route or each speed profile of each of the plurality of target movement plan may be different. The user may choose one from the plurality of target movement plans based on his/her own will/purpose. For example, if the user is a professional runner, the user may choose a target movement plan of which speeds may be relativity faster. As another example, if the user likes jogging, he/she may choose a target movement plan of which speeds may be relatively slower.

In some embodiments, the autonomous companion unit 120 may determine the target movement plan based on a purpose for performing the physical activity. For example, if the user is a more proficient runner, the autonomous companion unit 120 may set the target movement plan with a longer distance, and faster speeds. As another example, if the user wants to jog, the autonomous companion unit 120 may set the target movement plan with lower speeds.

In some embodiments, the autonomous companion unit 120 may receive user instructions. For example, the user instruction may include pausing the physical activity, continuing the physical activity, broadcasting the performance information, shifting control of the system, forcibly change the movement plan, etc. In some embodiments, the autonomous companion unit 120 may further encourage praise, prize, evaluate, or critic the user based on the performance of the user, so that the user may preserve.

In some embodiments, the autonomous companion unit 120 may be in communication with one or more components of the physical activity assistance system 100 (e.g., the body condition monitoring unit 110, or the physical activity management unit 130) via the network 140. For example, the autonomous companion unit 120 may obtain the body condition data from the body condition monitoring unit 110 via the network 140.

In some embodiments, the autonomous companion unit 120 may be directly in communication with the body condition monitoring unit 110. In certain embodiments, the autonomous companion unit 120 communicates with the body condition monitoring 110 unit via a wired connection, e.g. using an electrical cable, an optical cable, a telephone wire, or the like, or any combination thereof. Preferably, the autonomous companion unit 120 communicates with the body condition monitoring unit 110 wirelessly, e.g. by using an intranet, a local area network (LAN), a wireless local area network (WLAN), a Bluetooth network, a ZigBee network, or a near field communication (NFC) network. In certain embodiments, the connection is via a Bluetooth connection between the autonomous companion unit 120 communicates with the body condition monitoring 110 unit.

In some embodiments, the autonomous companion unit 120 may be an autonomous device or a semi-autonomous device, e.g., a robot, an autonomous airplane, an autonomous mini-vehicle. The autonomous device or the semi-autonomous device may perform a set of instructions to implement the functions and/or methods described in the present disclosure.

The physical activity management unit 130 may be configured to determine the preliminary movement plan. The preliminary movement plan may be customized for the user or by others (e.g. a trainer of the user). In some embodiments, the preliminary movement plan may be determined based on personal information of the user, the preliminary body condition data when the user performs the physical activity and preliminary surroundings data when the user performs the physical activity. For example, the personal information may include an age, a height, a weight, or a gender of the user, an occupation, a recorded proficiency when the user performs the physical activity, etc. More detailed description of determining the preliminary movement plan can be found elsewhere in the present disclosure, e.g., FIG. 6 and the descriptions thereof.

In some embodiments, the physical activity management unit 130 may be in communication with one or more components of the physical activity assistance system 100 (e.g., the body condition monitoring unit 110 or the autonomous companion unit 120) via the network 140.

In some embodiments, the physical activity management unit 130 may be an application installed on a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an internetphone, or the like, or any combination thereof. In some embodiments, the wearable device may include a smart bracelet, a smart footgear, a smart glass, a smart helmet, a smart watch, a smart clothing, a smart backpack, a smart accessory, or the like, or any combination thereof. In some embodiments, the smart mobile device may include a smartphone, a personal digital assistance (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass™, an Oculus Rift™, a Hololens™, a Gear VR™, etc. In some embodiments, the physical activity management unit 130 may be integrated in the body condition monitoring unit 110.

The network 140 may facilitate exchange of information and/or data. In some embodiments, one or more components of the physical activity assistance system 100 (e.g., the autonomous companion unit 120, the body condition monitoring unit 110, or the physical activity management unit 130) may transmit information and/or data to other component(s) of the physical activity assistance system 100 via the network 140. For example, the autonomous companion unit 110 may obtain body condition data of a user from the body condition monitoring unit 120 via the network 140. In some embodiments, the network 140 may be any type of wireless network. Merely by way of example, the network 140 may include, an intranet, an Internet, a local area network (LAN), a wide area network (WAN), a wireless local area network (WLAN), a metropolitan area network (MAN), a Bluetooth network, a ZigBee network, a near field communication (NFC) network, or the like, or any combination thereof. In some embodiments, the network 140 may include one or more network access points. For example, the network 140 may include wireless network access points such as base stations and/or internet exchange points 120-1, 120-2, . . . , through which one or more components of the physical activity assistance system 100 may be connected to the network 140 to exchange data and/or information.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the physical activity magnet unit 130 may be omitted, and the functions thereof may be implemented by other components of the physical activity assistance system 100 (e.g., the autonomous companion unit 120). As another example, at least a portion functions of the autonomous companion unit 120 may be implemented by a remote processing device (e.g., the physical activity management unit 130, the body condition monitoring unit 110).

FIG. 2 is a block diagram illustrating an exemplary autonomous companion unit according to some embodiments of the present disclosure. The autonomous companion unit 110 may include a transporting subunit 210, a plurality of sensors 220, a controller subunit 230, and an interaction subunit 240.

The transporting subunit 210 may be configured to enable the movement of the autonomous companion unit 120. The transporting subunit 210 may enable the autonomous companion unit 120 to move along any direction, e.g., a right direction, a left direction, a forward direction, a backward direction, etc. In some embodiments, the transporting subunit 210 may include wheels that can be used to move the autonomous companion unit 120. For example, the transporting subunit 210 may include the moving components of a self-balancing vehicle. In some embodiments, the transporting subunit 210 may allow the autonomous companion unit 120 to simulate the movement of a human being. In some embodiments, the transporting subunit 210 may further enable the autonomous companion unit 120 to perform physical activities like the human being (e.g., the user).

The sensors 220 may be physically connected to the transporting subunit 210, and configured to obtain surroundings data associated with the autonomous companion unit 120. The sensors 220 may include a GPS sensor, an odometry sensor, an angle sensor, a depth camera, a high-definition camera, a Light Detection And Ranging (LiDAR), or the like, or any combination thereof. In some embodiments, the odometry sensor add/or the GPS sensor may be used to determine a relative distance to the surroundings object and locate the surroundings object. The depth camera, the high-definition camera may be used to obtain images of the surroundings object. The LiDAR may be used to obtain point clouds (e.g., three-dimensional representation) associated with the surroundings object. Therefore, the surroundings data associated with the autonomous companion unit 120 may then be determined by the sensors 220.

Taking running as an example, the surroundings data associated with the autonomous companion unit 120 may include data of surroundings objects associated with autonomous companion unit 120, environmental information associated with the surroundings. For example, the surroundings objects may include roads, traffic lights, traffic signs, temporary road blocks, pedestrians, landmarks, vehicles, trees, buildings, rivers, bridges, or the like, or any combination thereof. The environmental information may include weather (e.g., sunny, rainy, snowy), visibility conditions, traffic conditions, wind speeds, time of day, etc. In some embodiments, the data of the surroundings object may include a location of the surroundings object, a dimension of the surroundings object, an outline of the surroundings object and any other feature information used for representing the surroundings objects. Taking a road as an example, the data of each may include a direction of a road, a length of a load, a width of a road, a center line of a road, a border line of the road, an intersection of the road, a turning (e.g., a right turning, a left turning) of a road, a slope of a road, an angle of inclination of a slope, or the like, or any combination. It should be noted that the term "road" herein used may refer to any type of road (e.g. paved road, sidewalk or dirt road) or any route according to which a runner can pass. In some embodiments, the road refers to a route outside an area specific designed for exercising or racing (e.g. not in a track field or stadium).

Taking running as an example, since the autonomous companion unit 120 may run in companion with the user, the surrounding data associated with the autonomous companion unit 120 may be similar to the surroundings data associated with the user. Therefore, the surroundings data obtained by the sensors 220 may be considered as the surroundings data associated with the user. The surroundings data associated with the user may represent a practical scenario where the user performs the physical activity.

In some embodiments, the sensors 220 may obtain performance information of the user. Taking running as an example, the performance information may include a current running speed of the user, a current speed of the user, a distance completed by the user, a remaining distance to be completed, or the like, or any combination thereof. In some embodiments, the autonomous companion unit 120 may encourage/remind the user based on the performance information. For example, if the user gives up, the autonomous companion unit 120 may encourage the user to insist. As another example, if the user surpasses a predetermined distance threshold, the user may prize the user and encourage the user to insist. As a further example, if the user runs slowly than the target movement plan, the autonomous companion unit 120 may remind the user or encourage the user to increase the speed.

The controller subunit 230 may be in communication with the transporting subunit 210 and the sensors 220. The controller subunit 230 may control the movement of the autonomous companion unit 120. In some embodiments, the controller subunit 230 may control the autonomous companion unit 120 to move according to a target movement plan. Taking running as an example, the target movement plan may include a target route and a target speed profile. The target route may refer to a route along which a user performs a physical activity. The target speed profile may include a plurality of speeds. The plurality of speeds may correspond to different segments of the target route.

In some embodiments, the controller subunit 230 may control the autonomous companion unit 120 to move according to the target movement plan based on computer vision technology. Specifically, the controller subunit 230 may obtain real-time images associated with the autonomous companion unit 120. The real-time images may show a realistic scenario when the autonomous companion unit 120 performs the physical activity in real-time. The controller subunit 230 may analyze and/or process the real-time images, and extract real-time information associated with the real-time images. For example, the real-time information may include a real-time speed of the autonomous companion unit 120, a real-time direction of the autonomous companion unit 120, a real-time surrounding environment, etc. The real-time information may be in a form that the controller subunit 230 can understand, e.g., numerical values, symbols, etc. The controller subunit 230 may determine whether to adjust the autonomous companion unit 120 to ensure it to move according to the target movement plan based on the real-time information. For example, if a real-time speed of the real-time information does not coincide with the target speed, the controller subunit 230 may determine to adjust the real-time speed of the autonomous companion unit 120 to the target speed. As another example, if a real-time direction of the real-time information coincides with the target route, the controller subunit 230 may determine to maintain the movement of the autonomous companion unit 120 and continue to monitor the autonomous companion unit 120.

In some embodiments, the controller subunit 230 may determine the target movement plan based on the body condition data, the surroundings data, and a preliminary movement plan. In some embodiments, the preliminary movement plan may be customized for the user or by others (e.g. a trainer of the user). The preliminary plan may be determined based on a template movement plan, preliminary user input, or the preliminary surroundings data. The template movement plan may be determined based on personal information of the user. The personal information of the user may include an age, a height, a weight, a gender, an occupation, a recorded proficiency when the user performs the physical activity, or the like, or any combination thereof. The preliminary user input may include an input speed profile, an input distance, an input running pace, or the like, or any combination. More detailed description of determining the preliminary movement plan can be found elsewhere in the present disclosure, e.g., FIG. 6 and the descriptions thereof.

In some embodiments, the controller subunit 230 may adjust the preliminary movement plan based on target body condition data and target surroundings data obtained when the user performs the physical activity according to the target movement plan to generate the target route. In some embodiments, the target body condition data and/or the target surroundings data may be different from the preliminary body condition data and/or the preliminary surroundings data respectively. The controller subunit 230 may automatically adjust the preliminary movement plan based on the difference. Alternatively, the controller subunit 230 may display the difference via an interface of the autonomous companion unit 120 or transmit the difference to the body condition monitoring unit 110 or the physical activity management unit 130, and the user may determine whether to adjust the preliminary movement plan based on the difference.

In some embodiments, the controller subunit 230 may determine the target movement plan further based on target user inputs. For example, the target user inputs may include inputting a target value, inputting a target speed profile, etc. The interaction subunit 240 may be in communication with the transporting subunit 210, the sensors 220, and the controller subunit 230. The interaction subunit 240 may display contents. The content may include the digital map, the target movement plan, the performance information, the body condition data, etc.

In some embodiments, the interaction subunit 240 may interact with the user to inform the user about the target movement plan. In some embodiments the user may directly accept the target movement plan. In some embodiments, the user may modify the target movement plan via the interaction subunit 240. For example, the user may modify the target time, the target distance, the target speed profile, etc. In some embodiments, the interaction subunit 240 may receive user instructions from the user through the interaction subunit 240. For example, the user instruction may include may include starting the physical activity, pausing the physical activity, continuing the physical activity, finishing the physical activity, changing the target movement plan, broadcasting the performance information, shifting control of the system, forcibly change the movement plan, etc.

Figure 3:
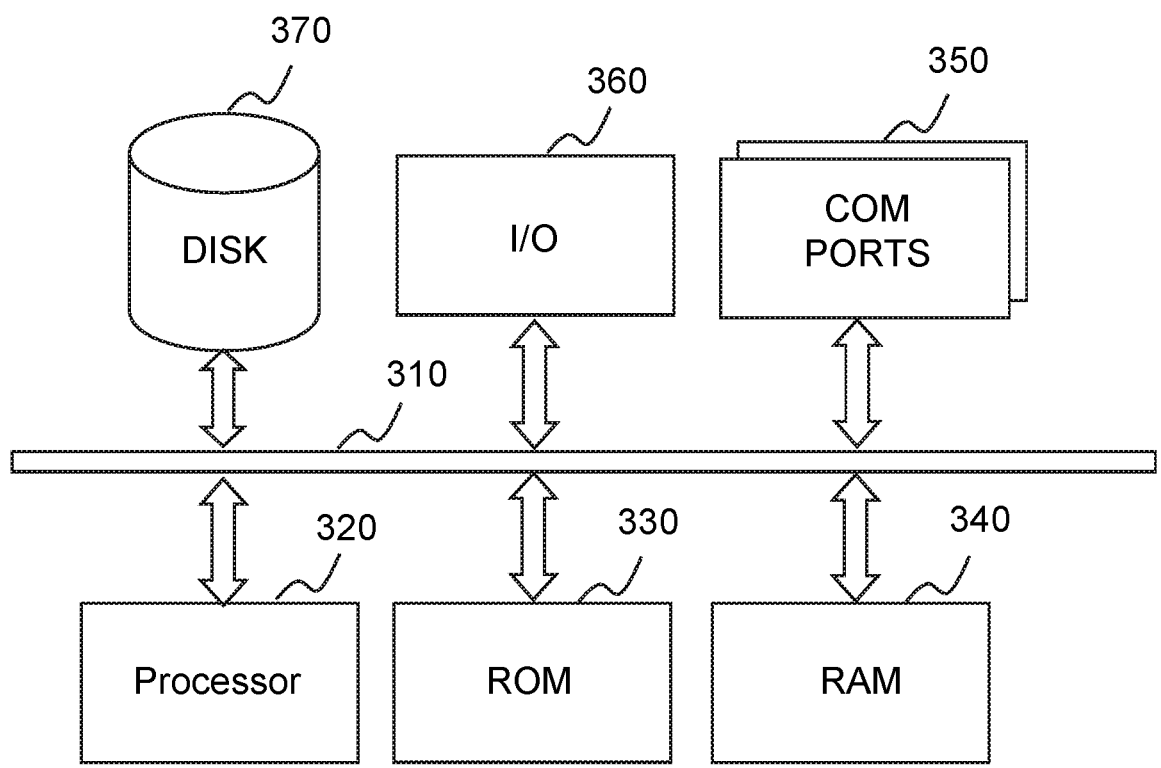
FIG. 3 is a schematic diagram illustrating exemplary hardware and/or software components of a computing device according to some embodiments of the present disclosure.

In some embodiments, the controller subunit 230 may be integrated in the autonomous companion unit 120. In some embodiments, the controller subunit 230 may be a mobile device (e.g., a mobile phone, a tablet computer) that can be separated from other parts of the autonomous companion unit 120. In some embodiments, the mobile device may be connected to the transporting subunit 210 via a wired connection or a wireless connection. For instance, the mobile device may be plugged directly onto the transporting subunit 210, or docked on a docking port of the transporting subunit 210. Merely by way of example, the wired connection may include an electrical cable, an optical cable, a telephone wire, or the like, or any combination thereof. The wireless connection may include a Bluetooth™ link, a Wi-Fi™ link, a WiMax™ link, a WLAN link, a ZigBee link, a mobile network link (e.g., 3G, 4G, 5G, etc.), or the like, or a combination thereof FIG. 3 is a schematic diagram illustrating exemplary hardware and/or software components of a computing device according to some embodiments of the present disclosure. In some embodiments, the body condition monitoring unit 110, the autonomous companion unit 120, and/or the physical activity management unit 130 may be implemented on the computing device 300. For example, the controller subunit 230 may be implemented on the computing device 300 and configured to perform functions of the controller subunit 230 disclosed in this disclosure.

The computing device 300 may be used to implement any component of the physical activity assistance system 100 as described herein. For example, the controller subunit 230 may be implemented on the computing device 300, via its hardware, software program, firmware, or a combination thereof. Although only one such computer is shown, for convenience, the computer functions relating to the physical activity assistance system 100 as described herein may be implemented in a distributed fashion on a number of similar platforms to distribute the processing load.

The computing device 300, for example, may include COM ports 350 connected to and from a network connected thereto to facilitate data communications. The computing device 300 may also include a processor 320, in the form of one or more processors (e.g., logic circuits), for executing program instructions. For example, the processor 320 may include interface circuits and processing circuits therein. The interface circuits may be configured to receive electronic signals from a bus 310, wherein the electronic signals encode structured data and/or instructions for the processing circuits to process. The processing circuits may conduct logic calculations, and then determine a conclusion, a result, and/or an instruction encoded as electronic signals. Then the interface circuits may send out the electronic signals from the processing circuits via the bus 310.

The computing device 300 may further include program storage and data storage of different forms including, for example, a disk 370, and a read only memory (ROM) 330, or a random access memory (RAM) 340, for various data files to be processed and/or transmitted by the computing device. The exemplary computer platform may also include program instructions stored in the ROM 330, RAM 340, and/or other type of non-transitory storage medium to be executed by the processor 320. The methods and/or processes of the present disclosure may be implemented as the program instructions. The computing device 300 also includes an I/O component 360, supporting input/output between the computer and other components. The computing device 300 may also receive programming and data via network communications.

Merely for illustration, only one processor is described in FIG. 3. Multiple processors are also contemplated, thus operations and/or method steps performed by one processor as described in the present disclosure may also be jointly or separately performed by the multiple processors. For example, if in the present disclosure the processor of the computing device 300 executes both step A and step B, it should be understood that step A and step B may also be performed by two different CPUs and/or processors jointly or separately in the computing device 300 (e.g., the first processor executes step A and the second processor executes step B, or the first and second processors jointly execute steps A and B).

Figure 4:
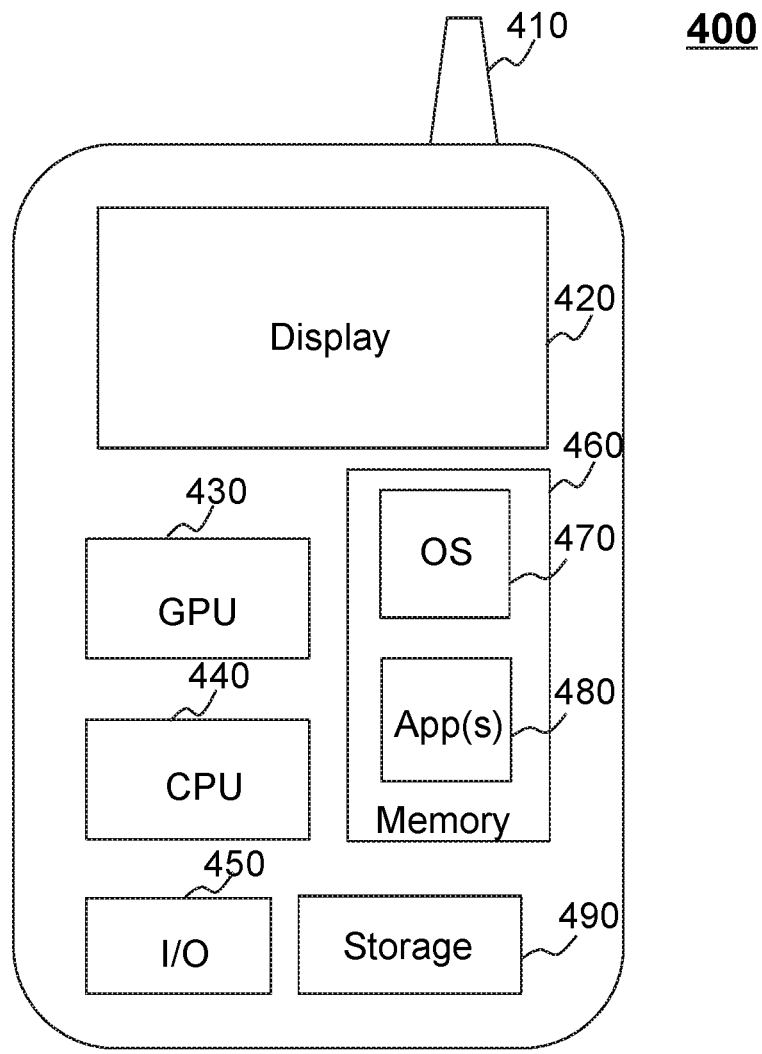
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device on which the body condition monitoring unit 110, the autonomous companion unit 120, or the physical activity management unit 130, may be implemented according to some embodiments of the present disclosure As illustrated in FIG. 4, the mobile device 400 may include a communication platform 410, a display 420, a graphic processing unit (GPU) 430, a central processing unit (CPU) 440, an I/O 450, a memory 460, a mobile operating system (OS) 470, and a storage 490. In some embodiments, any other suitable component, including but not limited to a system bus or a controller (not shown), may also be included in the mobile device 400.

In some embodiments, the mobile operating system 470 (e.g., iOS™, Android™, Windows Phone™, etc.) and one or more applications 480 may be loaded into the memory 460 from the storage 490 in order to be executed by the CPU 440. The applications 480 may include a browser or any other suitable mobile apps for receiving and rendering information relating to physical activities or other information from the physical activity assistance system 100. User interactions with the information stream may be achieved via the I/O 450 and provided to the autonomous companion unit 120 and/or other components of the physical activity assistance system 100 via the network 140.

Figure 5:
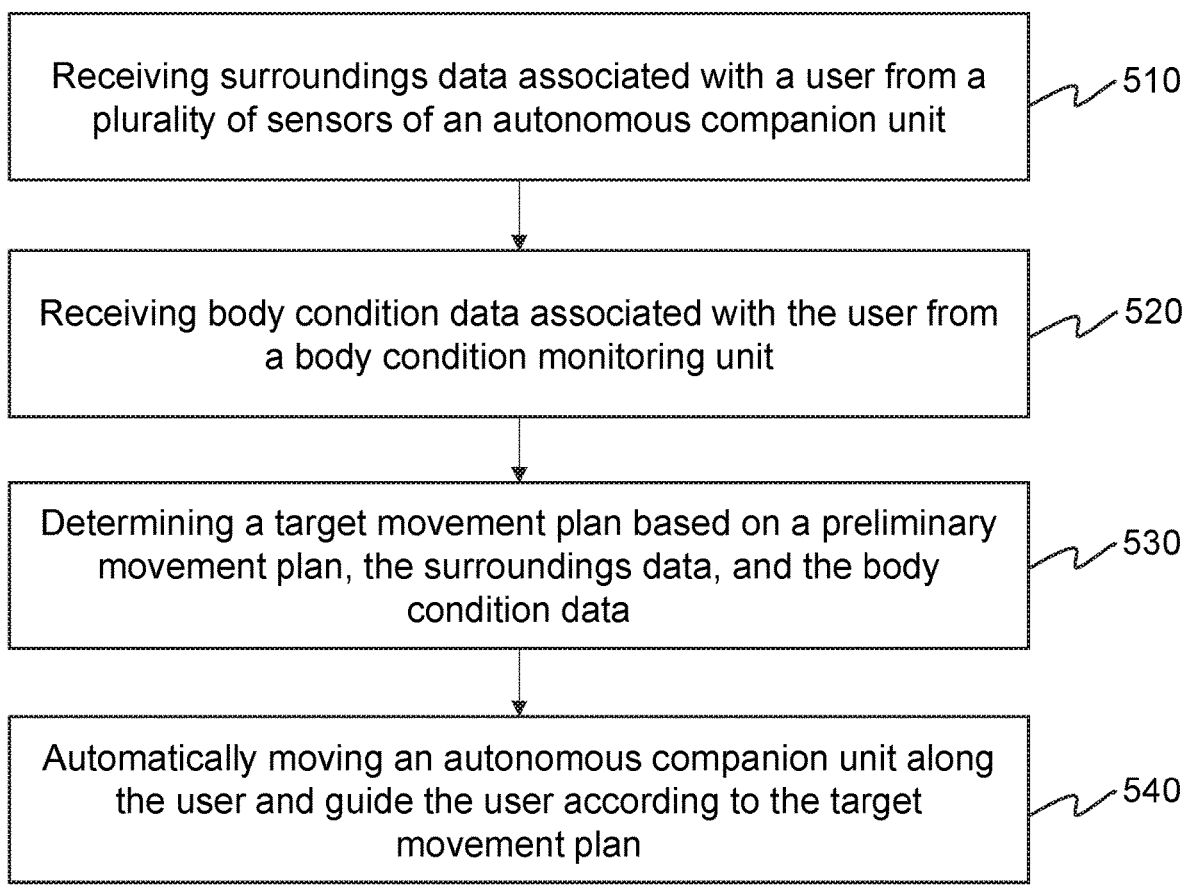
FIG. 5 is a flowchart illustrating an exemplary process for determining a target movement plan for automatically moving an autonomous companion unit along a user and guide the user according to some embodiments of the present disclosure.

FIG. 5 is a flowchart illustrating an exemplary process for determining a target movement plan for automatically moving an autonomous companion unit along a user and guide the user according to some embodiments of the present disclosure. In some embodiments, the process 500 may be implemented as a set of instructions (e.g., an application) stored in the storage ROM 330 or RAM 340. The processor 320 and/or the components in FIG. 3 may execute the set of instructions, and when executing the instructions, the processor 320 and/or the components may be configured to perform the process 500. The operations of the illustrated process presented below are intended to be illustrative. In some embodiments, the process 500 may be accomplished with one or more additional operations not described and/or without one or more of the operations herein discussed. Additionally, the order in which the operations of the process as illustrated in FIG. 5 and described below is not intended to be limiting.

In 510, the controller subunit 230 may receive surroundings data associated with a user from a plurality of sensors of the autonomous companion unit 120 as the user performs a physical activity. The surroundings data may represent a practical scenario where the user performs the physical activity. Taking running as an example, the surroundings data associated with the user may include data of surroundings objects associated with the user, environmental information associated with the surroundings. For example, the surroundings objects may include roads, traffic lights, traffic signs, temporary road blocks, pedestrians, landmarks, vehicles, trees, buildings, rivers, bridges, or the like, or any combination thereof. The environmental information may include weather (e.g., sunny, rainy, snowy), visibility conditions, traffic conditions, wind speeds, time of day, etc. In some embodiments, the data of the surroundings object may include a location of the surroundings object, a dimension of the surroundings object, an outline of the surroundings object and any other feature information used for representing the surroundings object. Taking a road as an example, the data of each may include a direction of a road, a length of a load, a width of a road, a center line of a road, a border line of the road, an intersection of the road, a turning (e.g., a right turning, a left turning) of a road, a slope of a road, an angle of inclination of a slope, or the like, or any combination.

In some embodiments, the plurality of sensors of the autonomous companion unit 120 may obtain surroundings data associated with the autonomous companion unit 120. Taking running as an example, since the autonomous companion unit 120 may run in companion with the user, the surroundings data associated with the autonomous companion unit 120 may be similar to the surroundings data associated with the user. Therefore, the surroundings data obtained by the plurality of sensors may be considered as the surroundings data associated with the user.

In some embodiments, the plurality of sensors may include a GPS sensor, an odometry sensor, an angle sensor, a depth camera, a high-definition camera, a Light Detection And Ranging (LiDAR), or the like, or any combination thereof. In some embodiments, the odometry sensor add/or the GPS sensor may be used to determine a relative distance to the surroundings object and locate the surroundings object. The depth camera, the high-definition camera may be used to obtain images of the surroundings object. The LiDAR may be used to obtain point clouds (e.g., three-dimensional representation) associated with the surroundings object. Therefore, the surroundings data associated with the autonomous companion unit 120 may then be determined by the plurality of sensors.

In some embodiments, the surroundings data may affect the performance of the physical activity of the user. Taking running as an example, an average running speed of the user along an upward slope may be slower than an average running speed of the user along a flat road segment. Therefore, in some embodiments, the surroundings data may be considered as a factor that may affect the user to perform the physical activity or performs the physical activity.

In some embodiments, the controller subunit 230 may generate a digital map of an area surrounding the autonomous companion unit 120 and/or the user at least based on the surroundings data. The digital map may represent the practical scenario where the user performs the physical activity. In some embodiments, the digital map may display the surroundings data associated with the user.

In 520, the controller subunit 230 may receive body condition data associated with the user from the body condition monitoring unit 110. The body condition data may indicate a physiological condition of the user when the user performs the physical activity. For example, the body condition data may include a heart rate, a blood pressure, a blood oxygen level, a blood sugar level, or the like, or any combination thereof.

In some embodiments, the body condition monitoring unit 110 may obtain the body condition data associated with the user. The body condition monitoring unit 110 may be directly in touch with the skin of the user or may be not in touch with the user, and may monitor the body condition data in real-time. In some embodiments, the body condition monitoring unit 110 may include a plurality of biometric sensors, and the plurality of the biometric sensors may measure the body condition data of the user in real time. For example, the plurality of biometric sensors may include a heart rate sensor (e.g., an optical transceiver), a blood pressure sensor (e.g., a photo plethysmography (PPG) sensor), a blood oxygen sensor (e.g., a pulse oximeter sensor), or the like, or any combination thereof.

The physical activity may affect the body condition data associated with the user. For example, body condition data obtained when the user run slowly may be different from body condition data obtained when the user runs fast. Therefore, in some embodiments, the body condition data may be considered as a factor that may affect the user to perform the physical activity or performs the physical activity.

In 530, the controller subunit 230 may determine a target movement plan based on a preliminary movement plan, the surroundings data, and the body condition data. The target movement plan may include a target route and a target speed profile. The target route may refer to a route along which a user performs a physical activity. The target speed profile may include a plurality of speeds. The plurality of speeds may correspond to different segments of the target route. A length of each segment may be different or the same. For example, a first segment (e.g., a first kilometer) of the target route may correspond to a first speed, a second segment (e.g., a second kilometer) of the target route may correspond to a second speed, and a third segment (e.g., a third kilogram) of the target route may correspond to a third speed. As another example, a first segment (e.g., 2 kilometers) of the target route may correspond to a first speed, a second segment (e.g., 1 kilometer) of the target route may correspond to a second speed, and a third segment (e.g., 1 kilogram) of the target route may correspond to a third speed.

In some embodiments, the preliminary movement plan may be customized for the user or by others (e.g. a trainer of the user). The preliminary plan may be determined based on a template movement plan, a preliminary user input, or the surroundings data obtained in 520. The template movement plan may be determined based on personal information of the user. The personal information of the user may include an age, a height, a weight, a gender, an occupation, a recorded proficiency when the user performs the physical activity, or the like, or any combination thereof. The preliminary user input may include an input speed profile, an input distance, an input running pace, or the like, or any combination. More detailed description of determining the preliminary movement plan can be found elsewhere in the present disclosure, e.g., FIG. 6 and the descriptions thereof.

In some embodiments, the controller subunit 230 may adjust the preliminary movement plan based on target body condition data and target surroundings data obtained when the user performs the physical activity according to the target movement plan to generate the target route. In some embodiments, the target body condition data and/or the target surroundings data may be different from the body condition data obtained in 520 and/or the surroundings data obtained in 510 respectively. The controller subunit 230 may automatically adjust the preliminary movement plan based on the difference. Alternatively, the controller subunit 230 may display the difference via an interface of the autonomous companion unit 120 or transmit the difference to the body condition monitoring unit 110 or the physical activity management unit 130, and the user may determine whether to adjust the preliminary movement plan based on the difference.

In some embodiments, the controller subunit 230 may determine the target movement plan further based on target user inputs. For example, the target user inputs may include inputting a target value, inputting a target speed profile, etc.

In 540, the controller subunit 230 may automatically move the autonomous companion unit 120 along the user and guide the user according to the target movement plan. In some embodiments, the autonomous companion unit 120 may perform the activity according to the target movement plan, and the user may perform the activity according to the target movement plan by following the autonomous companion unit 120.

In some embodiments, the controller subunit 230 may automatically move the autonomous companion unit 120 according to the target movement plan by controlling data associated with the autonomous companion unit 120. The data may include a speed, a location, a direction, a strength of the autonomous companion unit 120, etc. In some embodiments, the controller subunit 230 may obtain the data in real-time, and compare the data with predetermined data when the autonomous companion unit 120 moves according to the target movement plan. In response to a determination that the data do not match the predetermined data, the controller subunit 230 may adjust the data to the predetermined data in real-time.

In some embodiments, the autonomous companion unit 120 may automatically move according to the target movement plan based on a control technique. The control technique may include a PID (proportional-integral-derivative) control technique, a PD (proportional-derivative) control technique, a PI (proportional-integral) control technique, a neural network control techniques, a self-adaptive control technique, a variable structure control technique, a fuzzy control technique, or the like, or any combination thereof.

In some embodiments, the autonomous companion unit 120 may track performance information while the user performs the physical activity in companion with the autonomous companion unit 120. For example, the performance information may include a current running speed of the user, a current speed of the user, a distance completed by the user, a remaining distance to be completed, or the like, or any combination thereof. In some embodiments, the autonomous companion unit 120 may encourage/remind the user based on the performance information. For example, if the user gives up, the autonomous companion unit 120 may encourage the user to insist. As another example, if the user surpasses a predetermined distance threshold, the user may prize the user and encourage the user to insist. As a further example, if the user runs slowly than the target movement plan, the autonomous companion unit 120 may remind the user or encourage the user to increase the speed.

In some embodiments, the autonomous companion unit 120 may display contents associated with the physical activity through an interaction unit when the user performs the physical activity. For example, the contents may include the digital map and the performance information. In some embodiments, the controller sub unit 230 may broadcast at least a portion of the contents (e.g., the current speed, the distance completed by the user, the remaining distance to be completed) by voice, e.g., at a predetermined time interval.

In some embodiments, the autonomous companion unit 120 may receive user instructions from the user through the interaction subunit 240. For example, the user instruction may include starting the physical activity, pausing the physical activity, continuing the physical activity, finishing the physical activity, changing the target movement plan, broadcasting the performance information, shifting control of the system, forcibly change the movement plan, etc. In some embodiments, the autonomous companion unit 120 may transmit the user instructions to the physical activity management subunit 130. The physical activity management subunit 130 may implement the user instructions.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. Operations of process 500 implemented by the autonomous companion unit 120 may be an example and for illustration purpose, at least a portion of the operations of process 500 may be implemented by other components of the physical activity assistance system 100. For example, operation 510 and/or operation 530 may be implemented by a remote processing device (e.g., the physical activity management unit 130, the body condition monitoring unit 110)

Figure 6:
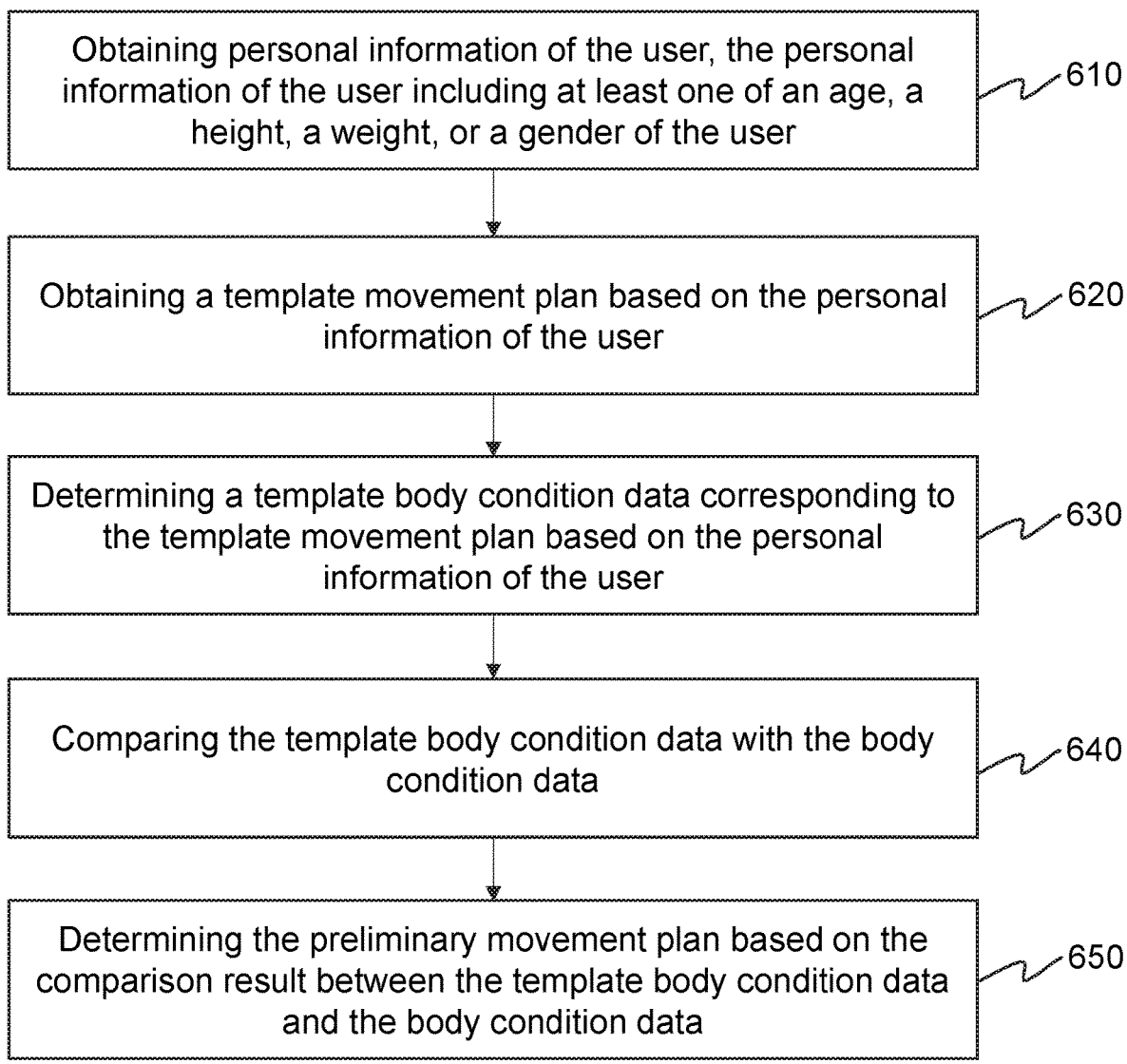
FIG. 6 is a flowchart illustrating an exemplary process for determining a preliminary movement plan according to some embodiments of the present disclosure.

FIG. 6 is a flowchart illustrating an exemplary process for determining a preliminary movement plan according to some embodiments of the present disclosure. In some embodiments, the process 600 may be implemented as a set of instructions (e.g., an application) stored in the storage ROM 330 or RAM 340. The processor 320 and/or the modules in FIG. 3 may execute the set of instructions, and when executing the instructions, the processor 320 and/or the modules may be configured to perform the process 600. The operations of the illustrated process presented below are intended to be illustrative. In some embodiments, the process 600 may be accomplished with one or more additional operations not described and/or without one or more of the operations herein discussed. Additionally, the order in which the operations of the process as illustrated in FIG. 6 and described below is not intended to be limiting.

In 610, the physical activity management unit 130 may obtain personal information of the user. For example, the personal information of the user may include an age, a height, a weight, a gender, an occupation, a recorded proficiency when the user performs the physical activity, or the like, or any combination thereof. In some embodiments, the user may input the personal information via an interface of the physical activity management unit 130. In some embodiments, the physical activity management unit 130 may obtain the personal information of the user from a third party entity (e.g., a database).

The personal information may be different for different users. In some embodiments, the personal information may be classified into a plurality of information categories. Each of the plurality of information categories may include users whose personal information satisfy a predetermined condition. For example, the predetermined condition may be that the gender is female, the age is within 20-30, and the weight is within 50-55 kilograms (the predetermined condition may also be referred to as a first predetermined condition). As another example, the predetermined condition may be that the gender is male, the age is within 20-30, and the weight is within 60-65 kilograms (the predetermined condition may also be referred to as a second predetermined condition). As a further example, the predetermined condition that the user is female and the user is an athlete (the predetermined condition may also be referred to as a third predetermined condition). Further, the physical activity management unit 130 may classify the user into one of the plurality of information categories based on the personal information. For example, if the gender of the user is female, the age is 25, and the weight is 50 kilograms, the user may be classified into the information category that satisfies the first predetermined condition.

In some embodiments, the physical activity management unit 130 may determine an information score, and the information score may indicate a comprehensive condition of the personal information. The physical activity management unit 130 may determine the information score based on empirical experiences, or a machine learning model. The information category and/or the information score may be used for further processing in process 600.

In 620, the physical activity management unit 130 may obtain a template movement plan based on the personal information of the user. The template movement plan may be used to instruct the user to perform the physical activity. In some embodiments, the template route may be a template route that the user moves along when the user performs the physical activity. Taking running as an example, the template movement plan may include a template route and a template speed profile. In some embodiments, the template route may be the same as the preliminary route described in operation 530. The template speed profile may include one or more template speeds determined based on the personal information when the user runs along the template route.

The template movement plan may be different due to different personal information. In some embodiments, the physical activity management unit 130 may obtain the template movement plan based on the information category and/or the information score. For example, the information category or the information may correspond to a reference speed profile. For example, for a user whose gender is female, age is within 20-30, and weight is within 50-55 kilograms, an average speed may be within a range of 7-8 min/km. As another example, for a user who runs infrequently, an average speed may be within a range of 5 min/km-7 min/km. As a further example, for a user whose gender is female and the user is a professional runner, an average speed may be within arrange of 3.2 min/km-3.4/km. The physical activity management unit 130 may further designate the corresponding reference speed profile as the template speed profile.

In 630, the physical activity management unit 130 may determine a template body condition data corresponding to the template movement plan based on the personal information of the user. The template body condition data may indicate to a body condition if the user performs the physical activity according to the template movement plan. For example, the template condition plan may include a heart rate, a blood pressure, a blood oxygen level, a blood sugar level, or the like, or any combination thereof.

In 640, the physical activity management unit 130 may compare the template body condition data with the body condition data. As described above, the template body condition data may be determined based on the template movement plan and the personal information, and the body condition data may be determined when the user actually performs the physical activity. Therefore, the template body condition data and the body condition data may be different or the same.

In 650, the physical activity management unit 130 may determine a preliminary movement plan based on the comparison result between the template body condition data and the body condition data. In response to a determination that the template body condition data is the same as the body condition data or a difference between the template body condition data and the body condition data is less than a predetermined threshold, the physical activity management unit 130 may designate the template movement plan as the preliminary movement plan. In response to a determination that the template body condition data is different from the body condition data, or the difference between the template body condition data and the body condition data is greater than the predetermined threshold, the physical activity management unit 130 may adjust the template movement plan based on the difference between the body condition data and the template body condition data. In some embodiments, if the body condition data is greater than the template body condition data, i.e., the user is more tired when the user actually performs the physical activity, the physical activity management unit 130 may decrease the plurality of template speeds to generate the preliminary speed profile based on the difference. Additionally or alternatively, the physical activity management unit 130 may decrease the template distance to generate the preliminary distance based on the difference.

In some embodiments, the physical activity management unit 130 may determine the preliminary plan based on preliminary user input via an interface of the physical activity management unit 130. Taking running as an example, the preliminary user input may include an input speed profile, an input distance, an input running pace, or the like, or any combination.

It should be noted that the above description is provided for the purpose of illustration, and is not intended to limit the scope of the present disclosure. For persons having ordinary skills in the art, multiple variations and modifications may be made under the teaching of the present disclosure. However, those variations and modifications do not depart from the scope of the present disclosure.

Figure 7:
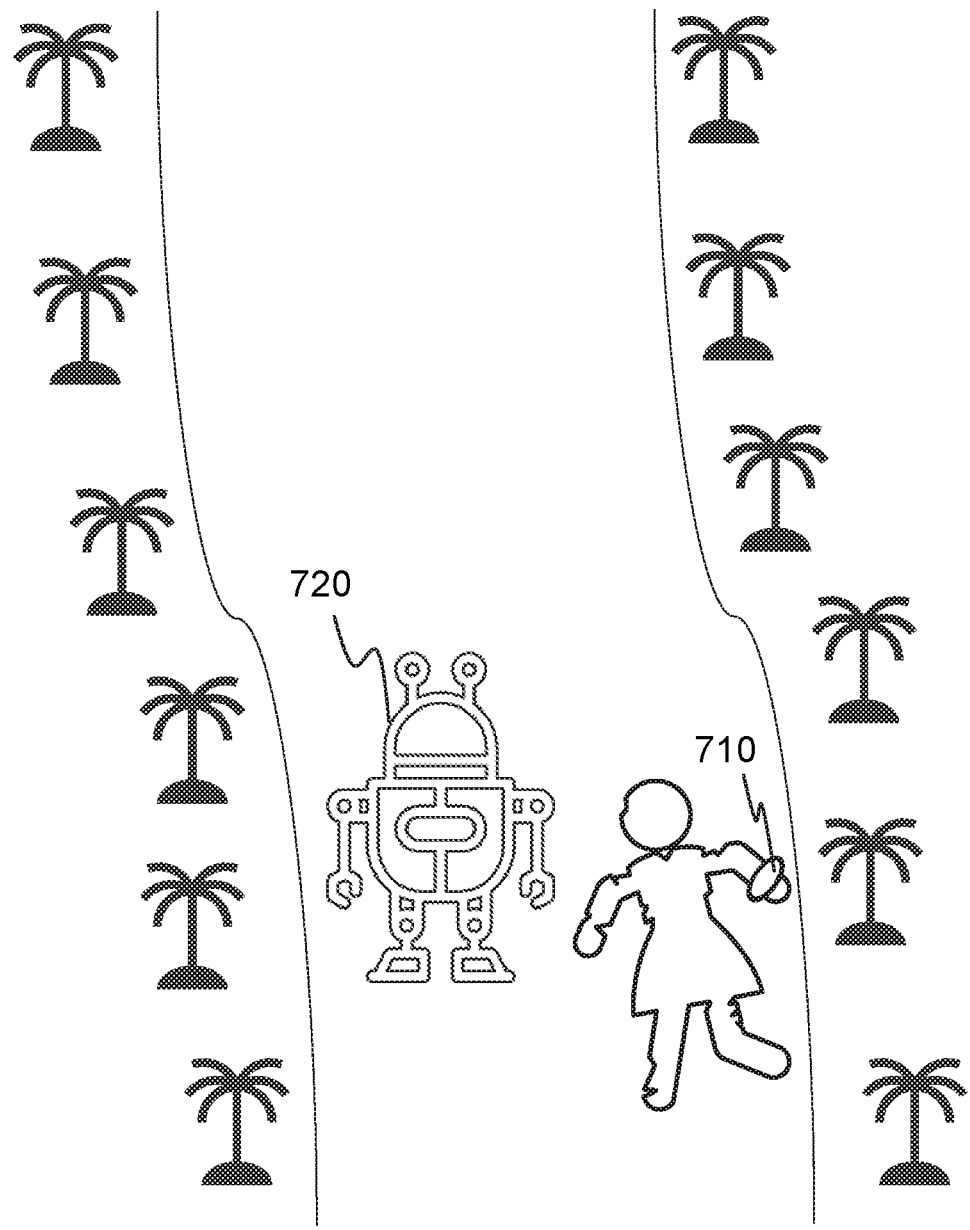
FIG. 7 is a schematic diagram illustrating an exemplary application scenario of a physical activity assistance system according to some embodiments of the present disclosure.

FIG. 7 is a schematic diagram illustrating an exemplary application scenario of a physical activity assistance system according to some embodiments of the present disclosure.

As described elsewhere in the present disclosure, the autonomous companion unit 120 may move alongside a user and guide the user to perform a physical activity. As illustrated in FIG. 7, a robot 720 represents the autonomous companion unit 120. The robot 720 runs outdoor in companion with the user.

As describe elsewhere in the present disclosure, body condition data associated with a user may be obtained by the body condition monitoring unit 110 while the user performs the physical activity. As illustrated in FIG. 7, a wearable device 710 mounted on the user's arm represents the body condition monitoring unit 110. The wearable device 710 obtains body condition data associated with the user in real-time.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

We claim:

1. An autonomous physical activity assistance system, comprising:
    a body condition monitoring unit configured to obtain body condition data of a user;
    an autonomous companion unit that is configured to automatically move alongside the user and guide the user, the autonomous companion unit comprising:
        a transporting subunit configured to enable the movement of the autonomous companion unit;
        a plurality of sensors physically connected to the transporting subunit, and configured to obtain surroundings data associated with the autonomous companion unit;
        a controller subunit in communication with the transporting subunit, the plurality of sensors, and the body condition monitoring unit, and configured to:
            receive the surroundings data from the plurality of sensors;
            wirelessly receive the body condition data from the body condition monitoring unit; and
            control the transporting subunit to move the autonomous companion unit according to a target movement plan, the target movement plan including a target route and a target speed profile, which are based on a preliminary movement plan, the surroundings data, and the body condition data; and
    a physical activity management unit configured to:
        obtain personal information of the user, the personal information of the user including at least one of an age, a height, a weight, or a gender of the user;
        determine an information score of the personal information of the user based on a machine learning model, the information score being a comprehensive condition of the personal information of the user;
        obtain a template movement plan based on the information score; and
        determine the preliminary movement plan based on the template movement plan.

2. The autonomous physical activity assistance system of claim 1, wherein the physical activity management unit is further configured to:
    provide the preliminary movement plan, which includes a preliminary route and a preliminary speed profile.

3. The autonomous physical activity assistance system of claim 2, wherein
    the surroundings data and the body condition data are obtained in real-time.

4. The autonomous physical activity assistance system of claim 2, wherein
    the controller subunit is further configured to adjust the preliminary route and the preliminary speed profile in real-time to provide the target route and target speed profile based on the surroundings data and the body condition data.

5. The autonomous physical activity assistance system of claim 1, wherein the physical activity management unit is further configured to store the target movement plan in a database.

6. The autonomous physical activity assistance system of claim 1, wherein:
the plurality of sensors include at least two or more of: a GPS sensor, an odometry sensor, a depth camera, or an angle sensor.

7. The autonomous physical activity assistance system of claim 6, wherein
the controller subunit or the physical activity management unit is further configured to determine a speed of the autonomous companion unit based on the surroundings data; and
the physical activity management unit is configured to determine the target movement plan based on the speed of the autonomous companion unit, the surroundings data and the body condition data.

8. The autonomous physical activity assistance system of claim 1, wherein
the controller unit or the physical activity management unit is further configured to generate a digital map of an area surrounding the autonomous companion unit based on the surroundings data.

9. The autonomous physical activity assistance system of claim 8, wherein:
the autonomous companion unit further comprises:
an interaction subunit, which is configured to display contents including the digital map.

10. The autonomous physical activity assistance system of claim 9, wherein
the interaction subunit is further configured to interact with the user to inform the user about the target movement plan.

11. The autonomous physical activity assistance system of claim 9, wherein
the controller subunit is further configured to receive user instructions from the user through the interaction subunit.

12. The autonomous physical activity assistance system of claim 11, wherein
the controller subunit is further configured to determine the target movement plan based on the preliminary movement plan, the surroundings data, the body condition data, and the user instruction.

13. The autonomous physical activity assistance system of claim 11, wherein the controller subunit is further configured to transmit the user instruction to the physical activity management unit.

14. The autonomous physical activity assistance system of claim 1, wherein the body condition data includes at least one of a heart rate, a blood pressure, a blood oxygen level, or a blood sugar level.

15. The autonomous physical activity assistance system of claim 2, wherein to provide the preliminary movement plan, the physical activity management unit is configured to:
determine a template body condition data corresponding to the template movement plan based on the personal information of the user;
compare the template body condition data with the body condition data; and
determine the preliminary movement plan based on the comparison result between the template body condition data and the body condition data.

16. The autonomous physical activity assistance system of claim 1, wherein the controller subunit includes a mobile device.

17. A method implemented on a computing device having at least one processor, at least one storage medium, and a communication platform connected to a network, the method comprising:
automatically moving an autonomous companion unit alongside a user and guide the user according to a target movement plan, wherein the target movement plan includes a target route and a target speed profile, and the target movement plan is determined by:
receiving surroundings data associated with the user from a plurality of sensors of the autonomous companion unit;
receiving body condition data associated with the user from a body condition monitoring unit; and
determining the target movement plan based on a preliminary movement plan, the surroundings data, and the body condition data, and the preliminary movement plan being determined by:
obtaining personal information of the user, the personal information of the user including at least one of an age, a height, a weight, or a gender of the user;
determining an information score of the personal information of the user based on a machine learning model, the information score being a comprehensive condition of the personal information of the user;
obtaining a template movement plan based on the information score; and
determining the preliminary movement plan based on the template movement plan.

18. The method of claim 17, further comprising:
providing the preliminary movement plan by a physical activity management unit, which includes a preliminary route and a preliminary speed profile;
receiving the surroundings data and the body condition data in real-time; and
adjusting the preliminary route and the preliminary speed profile in real-time to provide the target route and target speed profile based on the surroundings data and the body condition data.

19. The method of claim 17, further comprising:
determining a speed of the autonomous companion unit based on the surroundings data by a physical activity management unit;
determining the target movement plan based on the speed of the autonomous companion unit, the surroundings data and the body condition data;
generating a digital map of an area surrounding the autonomous companion unit based on the surroundings data;
displaying contents including the digital map;
interacting with the user to inform the user about the target movement plan;
receiving user instructions from the user; and
determining the target movement plan based on the preliminary movement plan, the surroundings data, the body condition data, and the user instruction.

20. The method of claim 18, wherein the providing the preliminary movement plan includes:
determining a template body condition data corresponding to the template movement plan based on the personal information of the user;
comparing the template body condition data with the body condition data; and determining the preliminary movement plan based on the comparison result between the template body condition data and the body condition data.

* * * * *